(12) United States Patent
Fojtik

(10) Patent No.: US 10,987,469 B2
(45) Date of Patent: Apr. 27, 2021

(54) ROTATABLE FINGER LOOP FOR SYRINGE, SYRINGE CONFIGURED TO RECEIVE THE ROTATABLE FINGER LOOP AND ASSOCIATED METHODS

(71) Applicant: PMT PARTNERS, LLC, Park City, UT (US)

(72) Inventor: Shawn P. Fojtik, Park City, UT (US)

(73) Assignee: PMT Partners, LLC, Park City, UT (US)

( * ) Notice: Subject to any disclaimer, the term of this patent is extended or adjusted under 35 U.S.C. 154(b) by 184 days.

(21) Appl. No.: 14/866,842

(22) Filed: Sep. 25, 2015

(65) Prior Publication Data
US 2016/0089497 A1    Mar. 31, 2016

Related U.S. Application Data

(60) Provisional application No. 62/055,441, filed on Sep. 25, 2014.

(51) Int. Cl.
*A61M 5/31* (2006.01)

(52) U.S. Cl.
CPC ... *A61M 5/3137* (2013.01); *A61M 2005/3139* (2013.01); *A61M 2207/00* (2013.01)

(58) Field of Classification Search
CPC ........ A61M 2005/3139; A61M 5/3137; A61M 2005/3142
USPC ....................................................... 604/227
See application file for complete search history.

(56) References Cited

U.S. PATENT DOCUMENTS

| | | | |
|---|---|---|---|
| 530,187 | A | 12/1894 | Laskey |
| 870,573 | A | 11/1907 | Myers |
| 901,567 | A | 10/1908 | Utschig |
| 1,019,207 | A | 3/1912 | Ward |

(Continued)

FOREIGN PATENT DOCUMENTS

| | | |
|---|---|---|
| DE | 19647529 | 5/1998 |
| DE | 19732332 | 2/1999 |

(Continued)

OTHER PUBLICATIONS

United Staes Patent and Trademark Office as the International Searching Authority, "International Search Report," for International Application No. PCT/US2008/061345, dated Sep. 16, 2008.

(Continued)

*Primary Examiner* — Rebecca E Eisenberg
*Assistant Examiner* — John A Doubrava
(74) *Attorney, Agent, or Firm* — Dentons Durham Jones Pinegar

(57) ABSTRACT

Finger control handles for conventional syringes are disclosed. The finger control handles may be configured to be assembled with a hand-held syringe, to be secured in place on a proximal portion of the barrel of the syringe and, when secured in place, to rotate freely about a circumference of the proximal portion of the barrel of the syringe. Systems that include the finger control handles and a hand-held syringe that is configured to capture the finger control handles are also disclosed, as are various methods of use, including methods for assembling the finger control handles with the syringe and methods for connecting the syringe to an elongated medical instrument, such as a catheter.

8 Claims, 4 Drawing Sheets

(56) References Cited

U.S. PATENT DOCUMENTS

| | | | |
|---|---|---|---|
| 1,218,513 A | 3/1917 | Biron | |
| 1,331,805 A | 2/1920 | Chance | |
| 1,453,418 A * | 5/1923 | Tessmer | A61M 5/31513 |
| | | | 604/222 |
| 1,718,596 A | 6/1929 | Smith | |
| 1,893,488 A | 1/1933 | Alexander | |
| 2,532,598 A * | 12/1950 | Boeger | A61M 5/00 |
| | | | 604/113 |
| 2,687,725 A | 8/1954 | Hein, Jr. | |
| 2,748,767 A | 6/1956 | Wright | |
| 2,904,043 A | 9/1959 | Friedman | |
| 3,016,897 A | 1/1962 | Kendrick | |
| 3,110,310 A | 11/1963 | Cislak | |
| 3,150,801 A | 9/1964 | Hamilton | |
| 3,212,685 A | 10/1965 | Swan et al. | |
| 3,281,023 A | 10/1966 | Bruck et al. | |
| 3,598,293 A | 8/1971 | Lee | |
| 3,770,169 A | 11/1973 | Roach | |
| 3,815,785 A | 6/1974 | Gilmont | |
| 3,840,007 A | 10/1974 | Fish | |
| 4,020,838 A | 5/1977 | Phillips et al. | |
| 4,065,034 A | 12/1977 | Callan | |
| 4,173,225 A | 11/1979 | Newman | |
| 4,187,849 A | 2/1980 | Stim | |
| 4,204,539 A | 5/1980 | Van Brugge | |
| 4,330,070 A | 5/1982 | Doubleday | |
| 4,364,388 A | 12/1982 | Cech | |
| 4,368,731 A | 1/1983 | Schramm | |
| 4,425,121 A | 1/1984 | Young et al. | |
| RE32,214 E | 7/1986 | Schramm | |
| 4,712,545 A | 12/1987 | Honkanen | |
| 4,738,664 A | 4/1988 | Prindle | |
| 4,744,789 A | 5/1988 | Johnson | |
| 4,808,165 A | 2/1989 | Carr | |
| 4,832,692 A | 5/1989 | Box et al. | |
| 4,861,339 A | 8/1989 | Jonischkeit | |
| 4,917,679 A | 4/1990 | Kronner | |
| 4,923,096 A | 5/1990 | Ennis, III | |
| 4,968,303 A | 11/1990 | Clarke et al. | |
| 4,994,065 A | 2/1991 | Gibbs et al. | |
| 5,027,605 A | 7/1991 | Hardesty | |
| 5,037,399 A | 8/1991 | Reichert et al. | |
| 5,045,066 A | 9/1991 | Scheuble et al. | |
| 5,069,421 A | 12/1991 | Kishi et al. | |
| 5,078,690 A | 1/1992 | Ryan | |
| 5,112,307 A | 5/1992 | Haber et al. | |
| 5,123,768 A | 6/1992 | Franklin | |
| 5,133,483 A | 7/1992 | Buckles | |
| 5,135,507 A | 8/1992 | Haber et al. | |
| 5,139,488 A | 8/1992 | Klein | |
| 5,150,488 A | 9/1992 | Yuan et al. | |
| 5,176,647 A | 1/1993 | Knoepfler | |
| 5,188,610 A | 2/1993 | Rains | |
| 5,209,732 A | 5/1993 | Lamprpoulos et al. | |
| 5,213,115 A | 5/1993 | Zytkovicz et al. | |
| 5,228,883 A | 7/1993 | Blakely et al. | |
| 5,279,563 A | 1/1994 | Brucker et al. | |
| 5,288,285 A | 2/1994 | Carter | |
| 5,304,147 A | 4/1994 | Johnson et al. | |
| 5,306,147 A | 4/1994 | Dragan et al. | |
| 5,306,248 A | 4/1994 | Barrington | |
| 5,308,358 A | 5/1994 | Bond et al. | |
| 5,336,201 A | 8/1994 | von der Decken | |
| 5,336,238 A | 8/1994 | Holmes et al. | |
| 5,350,365 A | 9/1994 | De Godoy Moreira | |
| 5,368,202 A | 11/1994 | Smrt | |
| 5,419,775 A * | 5/1995 | Haffner | A61M 5/3135 |
| | | | 604/187 |
| 5,425,743 A | 6/1995 | Nicholas | |
| 5,453,093 A * | 9/1995 | Haining | A61M 5/31511 |
| | | | 604/110 |
| 5,480,409 A | 1/1996 | Riza | |
| 5,499,998 A | 3/1996 | Meade | |
| 5,505,704 A | 4/1996 | Pawelka et al. | |
| 5,507,727 A | 4/1996 | Crainich | |
| 5,507,730 A | 4/1996 | Haber et al. | |
| 5,511,556 A | 4/1996 | De Santis | |
| 5,531,708 A | 7/1996 | Woodruff | |
| 5,560,373 A | 10/1996 | De Santis | |
| 5,562,655 A | 10/1996 | Mittelstadt et al. | |
| 5,591,135 A | 1/1997 | Sullivan | |
| 5,591,176 A | 1/1997 | Henderson et al. | |
| 5,645,561 A | 7/1997 | Smith et al. | |
| 5,685,862 A | 11/1997 | Mahurkar | |
| 5,692,642 A | 12/1997 | Brattesani | |
| 5,722,829 A | 3/1998 | Wilcox et al. | |
| 5,733,258 A | 3/1998 | Lane | |
| 5,733,259 A | 3/1998 | Valcke et al. | |
| 5,735,874 A | 4/1998 | Measamer et al. | |
| 5,749,968 A | 5/1998 | Melanson et al. | |
| 5,755,362 A | 5/1998 | Rodriguez, Jr. et al. | |
| 5,807,340 A | 9/1998 | Pokras | |
| 5,830,194 A | 11/1998 | Anwar et al. | |
| 5,851,214 A | 12/1998 | Larsen et al. | |
| 5,867,911 A | 2/1999 | Yates et al. | |
| 5,881,928 A | 3/1999 | Register et al. | |
| 5,893,488 A | 4/1999 | Hoag et al. | |
| 5,951,517 A | 9/1999 | Lampropoulos et al. | |
| 5,961,494 A | 10/1999 | Hogan | |
| 5,961,496 A | 10/1999 | Nielsen et al. | |
| 5,964,380 A | 10/1999 | Hazzard et al. | |
| 5,964,736 A | 10/1999 | Lane | |
| 5,992,694 A | 11/1999 | Keller | |
| 6,007,515 A | 12/1999 | Epstein et al. | |
| 6,024,728 A | 2/2000 | Schulz | |
| 6,030,368 A | 2/2000 | Anwar et al. | |
| 6,047,861 A | 4/2000 | Vidal et al. | |
| 6,080,136 A | 6/2000 | Trull et al. | |
| 6,095,814 A | 8/2000 | Petrich et al. | |
| 6,117,158 A | 9/2000 | Measamer et al. | |
| 6,161,982 A | 12/2000 | Cole | |
| 6,183,444 B1 | 2/2001 | Glines et al. | |
| 6,213,984 B1 | 4/2001 | Lane et al. | |
| 6,241,708 B1 | 6/2001 | Reilly et al. | |
| 6,264,637 B1 | 7/2001 | Hogan | |
| 6,280,401 B1 | 8/2001 | Mahurkar | |
| 6,368,307 B1 | 4/2002 | Ziemba et al. | |
| 6,406,460 B1 | 6/2002 | Hogan | |
| 6,439,439 B1 | 8/2002 | Rickard et al. | |
| 6,585,696 B2 | 7/2003 | Petersen et al. | |
| 6,607,512 B2 | 8/2003 | Oliver et al. | |
| 6,752,781 B2 | 6/2004 | Landau et al. | |
| 6,764,466 B1 | 7/2004 | Staats et al. | |
| 6,802,824 B2 | 10/2004 | Mickley et al. | |
| 6,858,696 B2 | 2/2005 | Destarac et al. | |
| 7,041,084 B2 | 5/2006 | Fojtik | |
| 7,097,636 B2 | 8/2006 | Pessin | |
| 7,125,395 B2 | 10/2006 | Hommann et al. | |
| 7,534,234 B2 | 5/2009 | Fojtik | |
| 7,591,604 B2 | 9/2009 | Roberts | |
| 7,617,569 B2 | 11/2009 | Liao | |
| 7,674,247 B2 | 3/2010 | Fojtik | |
| 7,988,677 B2 | 8/2011 | Fojtik | |
| 8,021,333 B2 | 9/2011 | Kaal et al. | |
| 8,539,644 B2 | 9/2013 | Fojtik | |
| 8,672,893 B2 | 3/2014 | Fojtik | |
| 10,058,656 B2 | 8/2018 | Fumiyama et al. | |
| 2002/0022805 A1 | 2/2002 | Lane | |
| 2002/0183698 A1 | 12/2002 | Quinn et al. | |
| 2003/0060777 A1 | 3/2003 | Benz et al. | |
| 2003/0078912 A1 | 4/2003 | Oliver et al. | |
| 2003/0139706 A1 | 7/2003 | Gray | |
| 2003/0187400 A1 | 10/2003 | Liao | |
| 2003/0195492 A1 | 10/2003 | Gobron et al. | |
| 2004/0044315 A1 * | 3/2004 | Ward, Jr. | A61B 5/153 |
| | | | 604/187 |
| 2004/0116873 A1 | 6/2004 | Fojtik | |
| 2004/0116893 A1 | 6/2004 | Spohn et al. | |
| 2004/0164097 A1 | 8/2004 | Orecchia et al. | |
| 2004/0166873 A1 | 8/2004 | Simic et al. | |
| 2004/0210200 A1 | 10/2004 | Gerondale et al. | |
| 2004/0247453 A1 | 12/2004 | Denolly | |
| 2005/0070848 A1 | 3/2005 | Kim et al. | |
| 2005/0070912 A1 | 3/2005 | Voellmicke | |

(56) References Cited

U.S. PATENT DOCUMENTS

| | | |
|---|---|---|
| 2005/0137575 A1 | 6/2005 | Thompson et al. |
| 2006/0247578 A1 | 11/2006 | Arguedas |
| 2006/0270996 A1 | 11/2006 | Fojtik |
| 2007/0010788 A1 | 1/2007 | Evans |
| 2007/0106226 A1 | 5/2007 | Croll et al. |
| 2007/0265573 A1 | 11/2007 | Fotik |
| 2008/0004703 A1 | 1/2008 | Trieu et al. |
| 2010/0217122 A1* | 8/2010 | Fumiyama ......... A61M 5/3129 600/432 |
| 2010/0268116 A1 | 10/2010 | Fojtik |
| 2011/0008750 A1 | 1/2011 | Dillard, III |
| 2011/0065992 A1 | 3/2011 | Bissinger |
| 2014/0200483 A1 | 7/2014 | Fojtik |

FOREIGN PATENT DOCUMENTS

| | | |
|---|---|---|
| EP | 0474218 | 3/1992 |
| EP | 0565045 | 10/1993 |
| EP | 0919251 | 6/1999 |
| EP | 1066797 | 7/2000 |
| EP | 1440706 | 7/2004 |
| EP | 1148834 | 4/2007 |
| EP | 1301227 | 11/2007 |
| FR | 2009514 | 2/1970 |
| FR | 2207728 | 6/1974 |
| FR | 2362638 | 3/1978 |
| FR | 2683140 | 5/1993 |
| FR | 2848860 B1 | 6/1994 |
| GB | 1456650 | 11/1976 |
| JP | S5948641 U1 | 3/1984 |
| JP | H01138370 U1 | 9/1989 |
| JP | H06296618 A | 10/1994 |
| JP | 0839471 | 2/1996 |
| JP | 2004527333 | 9/2004 |
| WO | 9908735 | 2/1999 |
| WO | 0044300 | 8/2000 |
| WO | 0207812 | 1/2002 |
| WO | 02094343 | 11/2002 |
| WO | 2004062713 | 7/2004 |
| WO | 2007133615 | 11/2007 |

OTHER PUBLICATIONS

European Patent Office as the International Searching Authority, "International Search Report and Written Opinion" issued in related International Application No. PCT/US2008/061239, dated Jul. 30, 2008.

European Patent Office, "Supplementary European Search Report," dated Jan. 15, 2015, in European patent application No. EP08780563.6.

Japanese Patent Office, "Notice of Reason for Rejection" dated Mar. 30, 2015, in Japanese patent application No. 2014-147359.

United States Patent and Trademark Office Acting as the International Searching Uthority, "International Search Report and Written Opinion," dated Dec. 28, 2015, in international application No. PCT/US2015/052506.

Gardiner, G.A., et al., "Selective Coronary Angiography Using a Power Injector," Am. J. Roentgenole pp. 831-833 (Apr. 1986).

Gruberg, A., et al., "Traditional Versus Automated Injection Contrast System in Diagnostic and Percutaneous Coronary Interventional Procedures: Comparison of the Contrast Volumn Delivered," J. Invasive Cardiol. 16(7): pp. 360-362 (Jul. 2004).

Call, J., et al., "Automated Contrast Injection in Contemporary Practice During Cardiac Catheterization and PCI: Effects on Contrast-Induced Nephrothapy," J. Invasive Cardiol. 18(10): pp. 469-471 (Oct. 2006).

Saito, T., et al., "Evaluation of New 4 French Catheters by Comparison to 6 French Coronary Artery Images," J. Invasive Cardiol. 11(1): pp. 13-30 (Jan. 1999).

European Patent Office as International Searching Authority, International Search Report and Written Opinion, International application No. PCT/US2008/061249, dated Jul. 29, 2008.

* cited by examiner

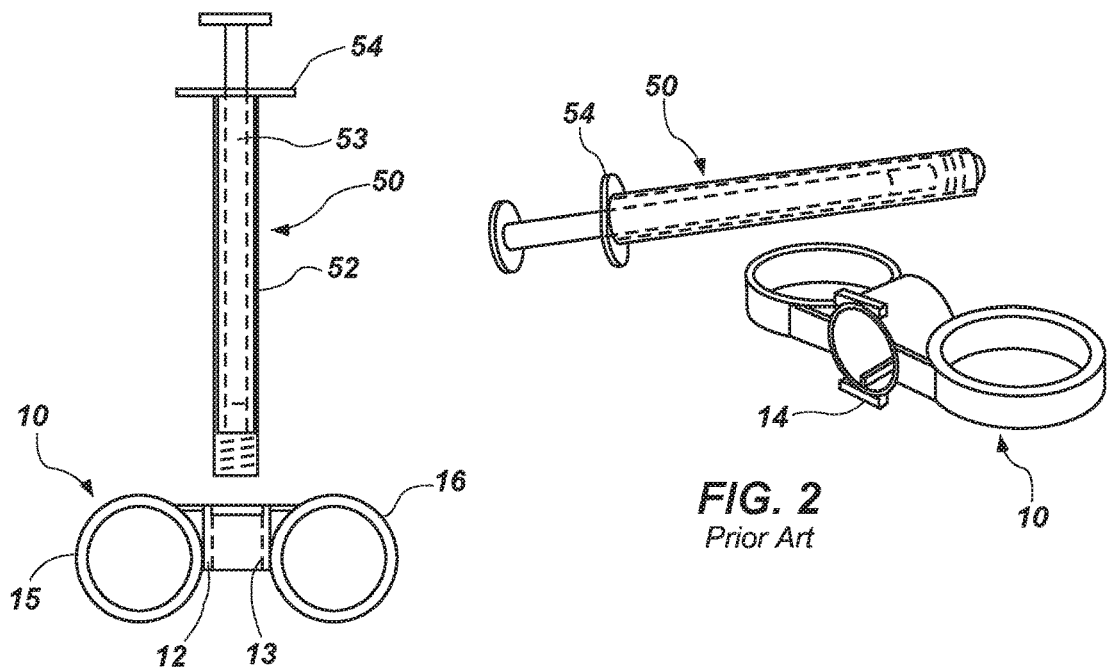
FIG. 1 *Prior Art*
FIG. 2 *Prior Art*
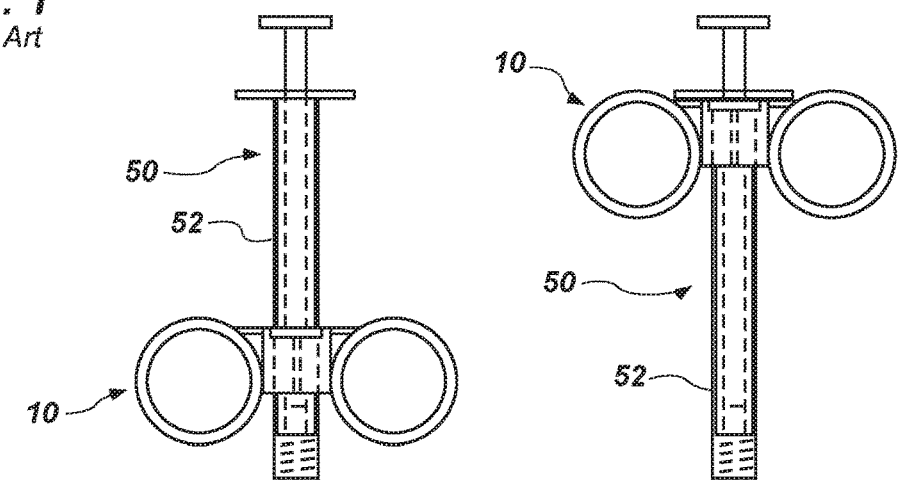
FIG. 3 *Prior Art*
FIG. 4 *Prior Art*
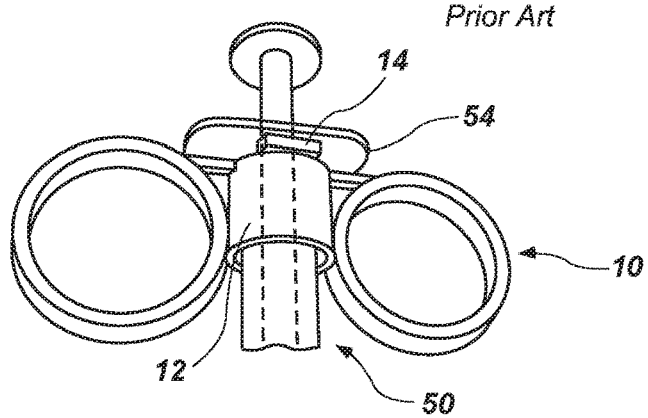
FIG. 5 *Prior Art*

ROTATABLE FINGER LOOP FOR SYRINGE, SYRINGE CONFIGURED TO RECEIVE THE ROTATABLE FINGER LOOP AND ASSOCIATED METHODS

CROSS-REFERENCE TO RELATED APPLICATION

A claim for the benefit of priority to the Sep. 25, 2014, filing date of U.S. Provisional Patent Application No. 62/055,441, titled SYRINGE WITH ROTATABLE HANDLE AND ASSOCIATED SYSTEMS AND METHODS ("the '041 Provisional Application"), is hereby made pursuant to 35 U.S.C. § 119(e). The entire disclosure of the '441 Provisional Application is incorporated herein by this reference.

TECHNICAL FIELD

This disclosure relates generally to finger control handles that are configured to be assembled with standard syringes, to syringes that are configured to receive finger control handles, and to systems that include a finger control handle and a syringe that will receive the finger control handle. More specifically, this disclosure relates to a finger control handle that is configured to receive the barrel of a syringe and, while in place on the barrel of the syringe, to rotate freely about a circumference of the barrel. Methods for assembling a finger control handle with the barrel of a syringe are also disclosed, as are methods for using syringes with rotatable finger control handles.

RELATED ART

As shown in FIGS. 1-5, an existing finger control handle 10, which includes finger loops 15 and 16, is configured to be assembled with the barrel 52 of a conventional syringe 50 (e.g., a 5 mL syringe, etc.) to enhance an individual's ability to control the conventional syringe 50 during use. In addition to a pair of finger loops 15 and 16, such a finger control handle 10 includes a body 12 between the finger loops 15 and 16, with a channel 13 extending through the body 12. The channel 13, which is configured to receive the barrel 52 of the conventional syringe 50, may have an inner diameter that will receive an outer diameter of the barrel 52, but tight tolerances enable the inner surface of the channel 13 to engage the outer surface of the barrel 52 by way of an interference fit as the finger control handle 10 is slid (see FIG. 3) onto a proximal location 53 on the outer surface of the barrel 52 (as shown in FIGS. 4 and 5). Once the finger control handle 10 is in place on a proximal location 53 of the barrel 52, it may be secured in place by the interference fit, by a snap fit (e.g., as inwardly, or centrally, protruding tabs 14 on the body 12 engage an outwardly, or radially, protruding flange 54 at a proximal end of the barrel 52, as seen in FIGS. 2 and 5, etc.) and/or by way of a bond (e.g., an adhesive bond, an ultrasonic weld, etc.). In any event, an orientation of the finger control handle 10 is fixed relative to an orientation of the barrel 52 of the conventional syringe 50 when the finger control handle 10 has been properly installed on the barrel 52; the finger control handle 10 will not rotate around the barrel 52.

When releasable means, such as an interference fit and/or tabs 14 are used to secure the finger control handle 10 to the barrel 52 of a conventional syringe 50, the finger control handle 10 may be removed from the barrel 52 by sliding the finger control handle 10 in a distal direction along the length of the barrel 52. Thus, the application of a distal force to the finger control handle 10 could easily dislodge the finger control handle 10 and enable the finger control handle 10 to move distally along the barrel 52. A distal force may be applied to the finger control handle 10 when the conventional syringe 50 is used to aspirate, which would undesirably cause the finger loop handle 10 to disengage the barrel 52.

When a syringe with a handle (e.g., a finger control handle 10, integral finger loops 15, 16, etc.) that has a fixed orientation relative to a circumference of a barrel of the syringe is used in conjunction with a catheter or another elongated medical instrument, the handle may impede a physician's or other healthcare worker's ability to couple the syringe to the catheter or other elongated instrument. For example, as the physician rotates the barrel of the syringe to couple it to the catheter, the handle may repeatedly hit the physician's hand, or the presence of the handle may require the physician to adjust the way he or she holds the syringe (often to a more uncomfortable position) as he or she couples the syringe to the catheter.

In addition, when a syringe with a handle that has a circumferentially fixed orientation relative to a barrel of the syringe is laid upon a flat surface, such as a table or tray, the handle may not lie flat against the surface, which may decrease the stability with which syringe is supported by the surface. When a syringe is not stably supported by a surface upon which it rests, it is more likely to be knocked off of the surface and, thus, contaminated, which may undesirably increase the complexity of a medical procedure in which the syringe is to be used or in which the syringe is used.

If a physician wants to be able to rotate a syringe with a handle having a circumferentially fixed orientation while using the syringe in connection with a catheter or another elongated medical instrument, the physician may use a rotatable luer lock connector to secure the syringe to the catheter. As many physicians will appreciate, the use of rotatable luer lock connectors is undesirable, as their multi-piece construction increases the likelihood that air may be introduced into the syringe and/or the catheter and, thus, into the body of a patient. In some circumstances, the introduction of air into a patient's body can be fatal.

SUMMARY

Finger control handles for a syringe may be configured to be assembled with a syringe that is hand-held and that is configured to be operated manually, or by hand. Such a finger control handle may also be referred to herein more simply as "handles" and as a "finger loop collar." The finger control handle may rotate freely around, or about, a circumference of the barrel of the syringe. In this regard, the finger control handle may reside upon a proximal portion of the barrel in a manner that aligns the handle coaxially with the barrel and that enables the handle to rotate around, or about, a circumference of the barrel.

The barrel of a syringe with which a finger control element according to this disclosure may be used may include a collar that protrudes beyond a primary circumference of the proximal portion of the barrel to retain a proximal side of the finger control handle, as well as one or more distal retention elements for retaining a distal side of the finger control handle. A distal retention element may comprise a tapered, or ramped, feature that tapers outwardly in a proximal direction and, at its proximal side, defines a distal boundary of the proximal portion of the barrel. The taper may be configured to enable assembly of a finger control handle with the barrel as the finger control handle is placed over a distal end of the barrel and forced toward a proximal end of the barrel, while the distal boundary prevents distal movement of the finger control handle after the finger control handle has been assembled with the barrel. Such a distal retention feature may extend around the entire circumference of the barrel, or it may include one or more sections that extend partially around the circumference of the barrel.

In some embodiments, the finger control handle may include flexible tabs that are configured to facilitate the introduction of the finger control handle over the distal retention feature of the barrel and, when the finger control handle is in place on a proximal portion of the barrel, to abut against the distal boundary defined by the distal retention feature(s) to prevent distal movement of the finger control handle off of the proximal portion of the barrel.

When the finger control handle is installed on the proximal portion of the barrel, the distal retention element(s) and a collar on a proximal side of the proximal portion of the barrel may limit longitudinal movement of the finger control handle and, therefore, may prevent removal of the finger control handle from the proximal portion of the barrel. In some embodiments, the distal retention element(s) of the barrel may hold the finger control handle in place on the proximal portion of the barrel while the syringe is used to generate a reduced pressure (e.g., a partial vacuum, etc.) or aspirate a sample, while the collar of the barrel may hold the finger control handle in place on the proximal portion of the barrel while the syringe is used to generate increased pressure or for injection or infusion.

Relative configurations of features of the finger control handle and the barrel that are associated with one another may enable the finger control handle to rotate freely about the proximal portion of the barrel. In a specific embodiment, a channel through the body of the finger control handle and the proximal portion of the barrel may have cylindrical shapes. A clearance between the outer diameter (OD) of the proximal portion of the barrel and the inner diameter (ID) of the channel through the body of the finger control handle may enable rotation of the finger control handle about the circumference of the barrel (e.g., coaxial rotation, about longitudinal axes through the channel and the barrel). In various embodiments, the difference between the ID of the channel and the OD of the proximal portion of the barrel may be about 0.010 inch or greater. The ability of the finger control handle to rotate freely about the proximal portion of the barrel of a syringe may enable a variety of functions, as disclosed in further detail hereinafter.

Other aspects, as well as features and advantages of various aspects, of the disclosed subject matter will become apparent to those of ordinary skill in the art through consideration of the ensuing description, the accompanying drawings and the appended claims.

BRIEF DESCRIPTION OF THE DRAWINGS

In the drawings,

FIGS. 1-5 illustrate features of an existing finger control handle and a conventional syringe with which the existing finger control handle is configured to be assembled;

DETAILED DESCRIPTION

Figure 6:
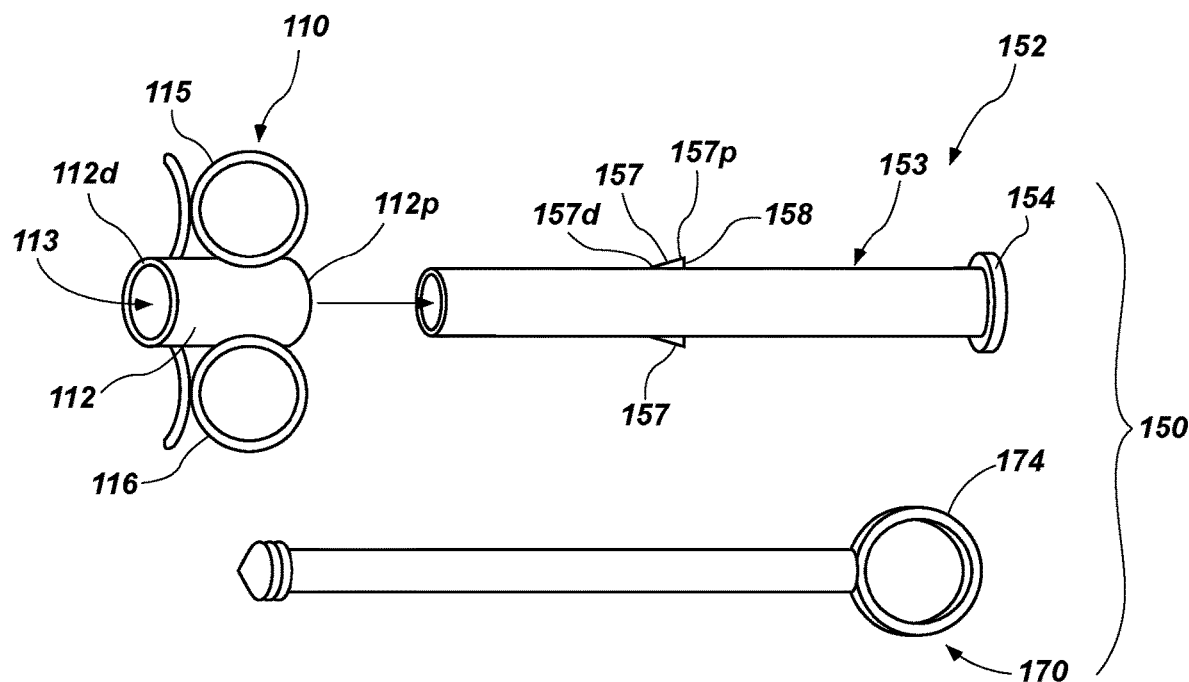
FIG. 6 provides an assembly view of an embodiment of a system according to this disclosure, which system includes a hand-held, hand-operated syringe with a barrel and a plunger, as well as a finger control handle that is configured to be assembled with the barrel of the syringe and to rotate about a circumference of the barrel, coaxially with the barrel.

Referring to FIG. 6, the elements of an embodiment of a system 100 for injecting fluids into the body of a subject and/or aspirating fluids from the body of a subject are illustrated. As shown, the system 100 includes a syringe 150 and a finger control handle 110.

The syringe 150 includes a barrel 152 and a plunger 170, with the plunger 170 being insertable into (distally) and removable from (proximally) the barrel 152. In specific, but non-limiting embodiments, the overall length of the barrel 152 of such a syringe 150 may be about 110 mm to about 140 mm. A proximal portion 153 of the barrel 152, which may be configured to receive and longitudinally retain the finger control handle 110, may have a length of about 30 mm. The distance a distal tip of the plunger 170 of the syringe 150 may move back and forth along the length of the barrel 152, or the stroke length of the syringe 150, may be about 55 mm to about 70 mm.

The syringe 150 may be configured to be held by an individual's hand (i.e., it may be hand-held) and operated with the individual's hand (i.e., hand-operated). More specifically, a collar 154 at a proximal end of the barrel 152 of the syringe 150 may have a larger circumference than the primary circumference of a remainder of the barrel 152. In some embodiments (such as that shown in FIGS. 1-5, but not the embodiment illustrated by FIG. 6), the collar 154 may be configured to receive two of the individual's fingers (e.g., his or her index and middle fingers, etc.). A proximal end 174 of the plunger 170 may be configured to receive the individual's thumb. In some embodiments, the proximal end 174 of the plunger 170 may be enlarged to enable an individual to press down on it (in a distal direction) with his or her thumb (see, e.g., FIGS. 1-5). In other embodiments, such as that depicted by FIG. 6, the proximal end 174 of the plunger 170 may comprise a thumb loop, which may facilitate both pushing (in a distal direction) and pulling (in a proximal direction) the plunger 170 respectively into and out of the barrel 152 of the syringe 150. An embodiment of the syringe 150 that includes a barrel 152 and a plunger 170 that are configured for manual operation may be used without a finger control handle 110, or a finger control handle 110 may be assembled with the barrel 152 to provide greater control and, in some embodiments, to better enable aspiration of fluids with the syringe 150.

Figure 7:
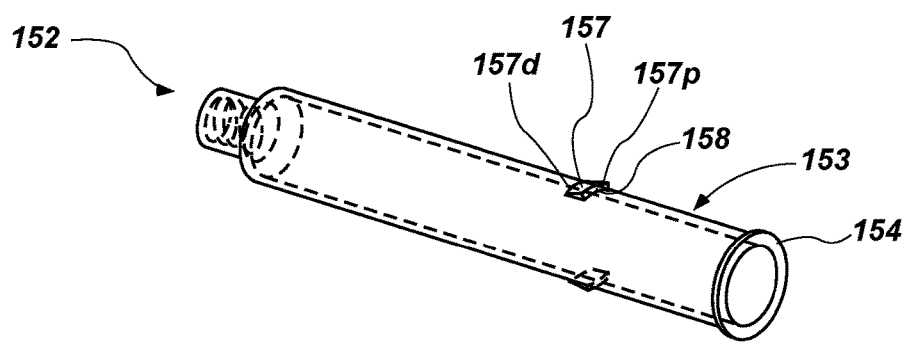
FIG. 7 is a perspective view of an embodiment of a barrel of a hand-held, hand-operated syringe, showing a ramped, or tapered, distal retention element for longitudinally retaining a distal side of a finger control handle at a proximal position on the barrel of the syringe and a circumferential collar for retaining a proximal side of the finger control handle at the proximal position on the barrel.

In some embodiments, such as that depicted by FIG. 7, the barrel 152 of the syringe 150 may lack a collar 154 that may be grasped by an individual's fingers. In such an embodiment, the barrel 152 (and, thus, the syringe 150) may be configured specifically for use with a finger control handle 110; i.e., the barrel 152 may not function without the finger control handle 110.

The finger control handle 110 is configured to be positioned on the barrel 152 of the syringe 150. More specifically, the finger control handle 110 includes a body 112 with a channel 113 that extends therethrough. The channel 113 is configured to receive a distal end 155 of the barrel 152 of the syringe 150, and a majority of the length of the barrel 152. As the body 112 of the finger control handle 110 and, thus, a remainder of the finger control handle 110 are slid proximally onto the barrel 152, the body 112 may slide over one or more distal retention elements 157 that protrude from a circumference of the barrel 152.

Figure 9:
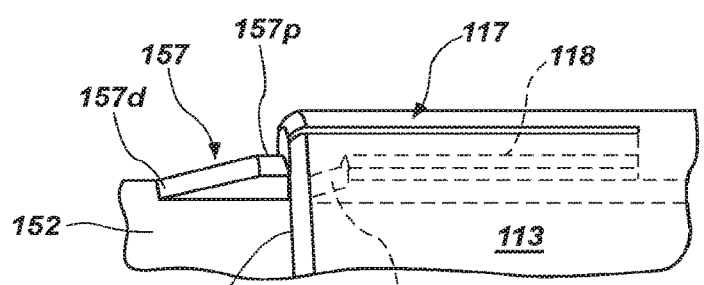
FIG. 9 illustrates an embodiment of the manner in which the embodiment of distal retention elements of the barrel shown in FIG. 7 of the embodiment of accommodation elements of the finger control handle shown in FIGS. 8A-8C interact with each other to facilitate assembly of the finger control handle with the barrel and retention of the finger control handle at the proximal position of the barrel.

As shown by FIGS. 6 and 7, the barrel 152 may include two relatively small, discrete distal retention elements 157 that are diametrically opposed to one another. As another option, more than two discrete distal retention elements 157 may be positioned at different radial positions around the circumference of the barrel 152. In other embodiments, a distal retention element 157 may extend farther around or even completely around the circumference of the barrel 152. A distal retention element 157 may comprise a tapered, or ramped, feature that tapers outwardly in a proximal direction and, at its proximal side, defines a distal boundary of the proximal portion 153 of the barrel 152. In the depicted embodiment, from its proximal side 157p to its distal side 157d, each distal retention element 157 tapers outwardly from a primary circumference of the barrel 152. As such, the distal retention element 157 includes an abutment 158 on its distal side 157d. This configuration may facilitate placement of the body 112 on a proximal portion 153 of the barrel 152, while retaining a distal side 112d of the body 112 and preventing the body 112 and the finger control handle 110 from unintentionally sliding distally off of the proximal portion 153 of the barrel 152, as illustrated by FIG. 9.

Figure 10:
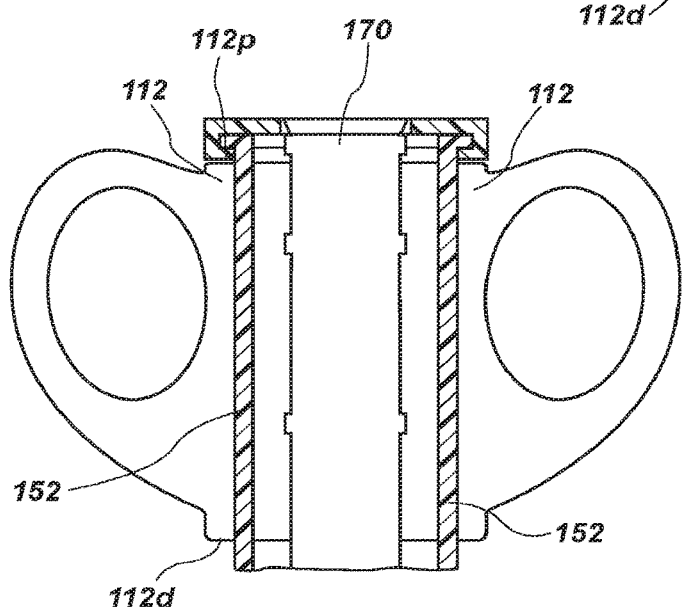
FIG. 10 provides a partial cross-sectional view of an embodiment of finger control handle on a proximal portion of the barrel of a syringe, as well as a portion of the plunger of the syringe inserted into the barrel.

A proximal side 112p of the body 112 may be held on the proximal portion 153 of the barrel 152 by the collar 154 at the proximal end of the barrel 152, as illustrated by FIG. 10. In some embodiments, the collar 154 may comprise an integral part of the barrel 152. In other embodiments, the collar 154 may be configured to snap into place on the proximal end of the barrel 152.

In some embodiments, with the possible exception of the distal side 112d and the proximal side 112p of the body 112, both of which comprise edges that are configured to be positioned against and to move relative to corresponding features (e.g., the abutment(s) 158 of the distal retention element(s) 157 of the barrel 152; a distal side 112d of the collar 154 at the proximal end of the barrel 152; etc.), no feature of the finger control handle 110 engages any feature of the barrel 152 of the syringe 150.

Figure 8A:
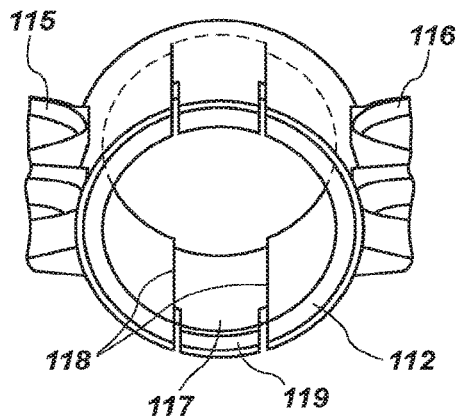
FIGS. 8A, 8B and 8C provide various perspectives of the body of an embodiment of a finger control handle according to this disclosure, showing accommodation elements that facilitate assembly of the finger control handle with the barrel of a syringe, as well as retention of the distal side of the finger control handle at the proximal position on the barrel.
Figure 8B:
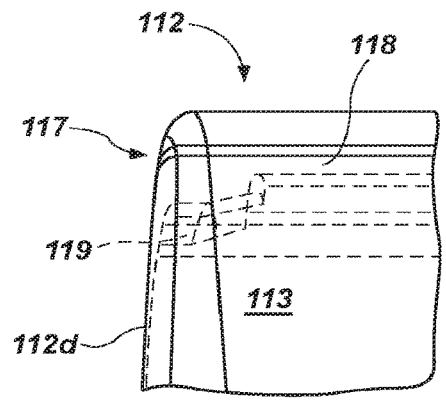
Figure 8C:
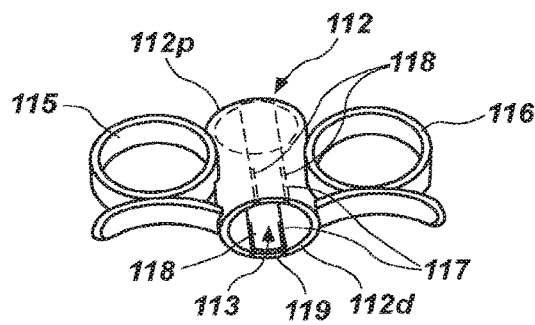

FIGS. 8A-8C and 9 show an additional feature that may be included in some embodiments of the body 112 of a finger control handle 110. In particular, FIGS. 8A-8C show that, in embodiments where the barrel 152 of a syringe 150 (FIGS. 6 and 7) with which the finger control handle 110 is to be assembled includes one or more discrete distal retention elements 157 (FIGS. 6 and 7), the body 112 may include a tab 117 that is positioned to accommodate each distal retention element 157. Each tab 117 is configured to accommodate a corresponding distal retention element 157 as the body 112 of the finger control handle 110 slides proximally onto the barrel 152 of the syringe 150. As illustrated, each tab 117 may be defined by a pair of longitudinal cuts 118 that extend from the distal side 112d of the body 112 to an intermediate location along the length of the body 112. Such a tab 117 may be configured (along with the material from which the body 112 is formed) to give way as it slides over a corresponding distal retention element 157 and to resiliently return to its original position after it has slid over the corresponding distal retention element 157. Once the tab 117 returns to its original position, its distal edge, along a distal side 112d of the remainder of the body 112, may prevent the body 112 and the finger control handle 110 from unintentionally sliding distally along the length of the barrel 152. Optionally, each tab 117 may include a protrusion 119 that faces inwardly, or centrally (i.e., into the channel 113 through the body 112) to further prevent unintentional distal sliding of the finger control handle 110 along the length of the barrel 152.

In addition, as should be apparent from FIGS. 8A-8C and 9, each tab 117 may enable the finger control handle 110 to be intentionally removed from the barrel 152 of a syringe 150 (FIGS. 6 and 7). For example, each tab 117 may be aligned with a corresponding distal retention element 157 (FIGS. 6 and 7) on the barrel 152 and pulled (radially) outward to enable the body 112 of the finger control handle 110 to slide distally off of the proximal portion 153 (FIGS. 6 and 7) of the barrel 152. Such a configuration may be useful in embodiments where the finger control handle 110 is intended to be reused.

Turning now to FIGS. 6 and 8C, in addition to the body 112, the finger control handle 110 may include a pair of finger loops 115 and 116 protruding from opposite sides of the body 112. Accordingly, the finger control handle 110 may also be referred to herein as a "finger loop collar." Each finger loop 115, 116 may be configured to receive an individuals' finger (e.g., his or her index finger and middle finger, etc.).

In various embodiments, the outer diameter (OD) of each finger loop 115, 116 may be about 25 mm to about 40 mm, while the inner diameter (ID), or opening size, of each finger loop 115, 116 may be about 20 mm to about 30 mm. The dimensions of the thumb loop, if any, at the proximal end 174 of the plunger 170 (FIG. 6) may be the same size or slightly larger than the corresponding dimensions of each finger loop 115, 116. Of course, other configurations of handles and plungers may also be used in connection with the barrel of a syringe according to this disclosure.

Figure 11A:
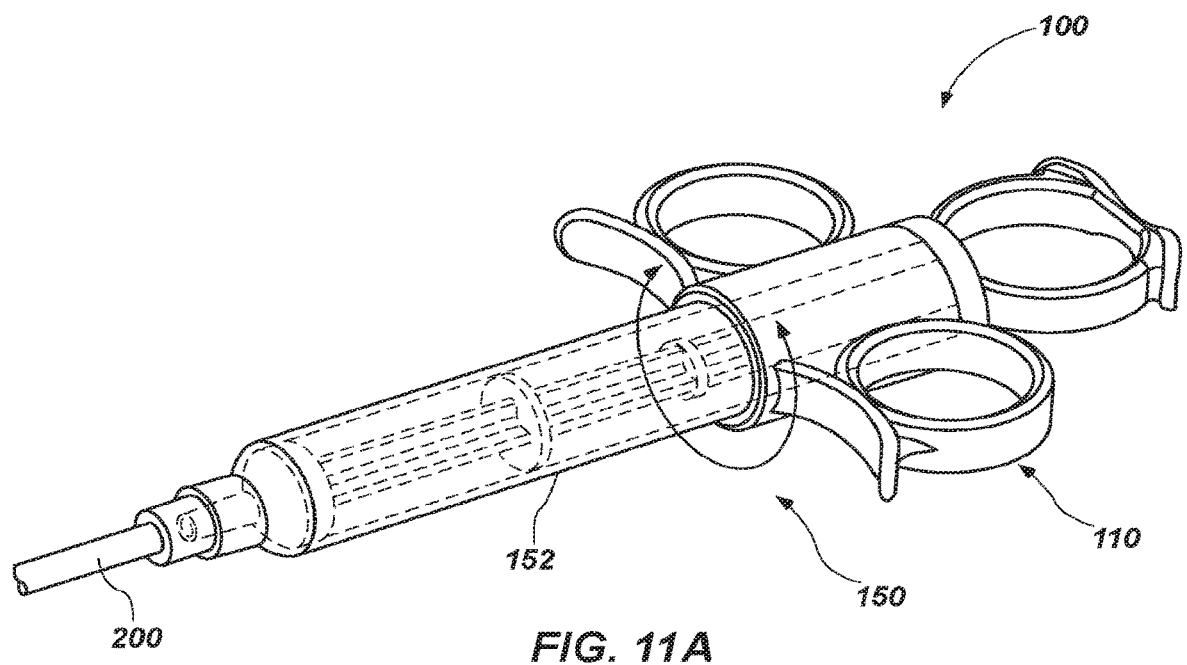
FIGS. 11A and 11B provide perspective views of a hand-held, hand-operated syringe to which a finger control handle has been assembled.
Figure 11B:
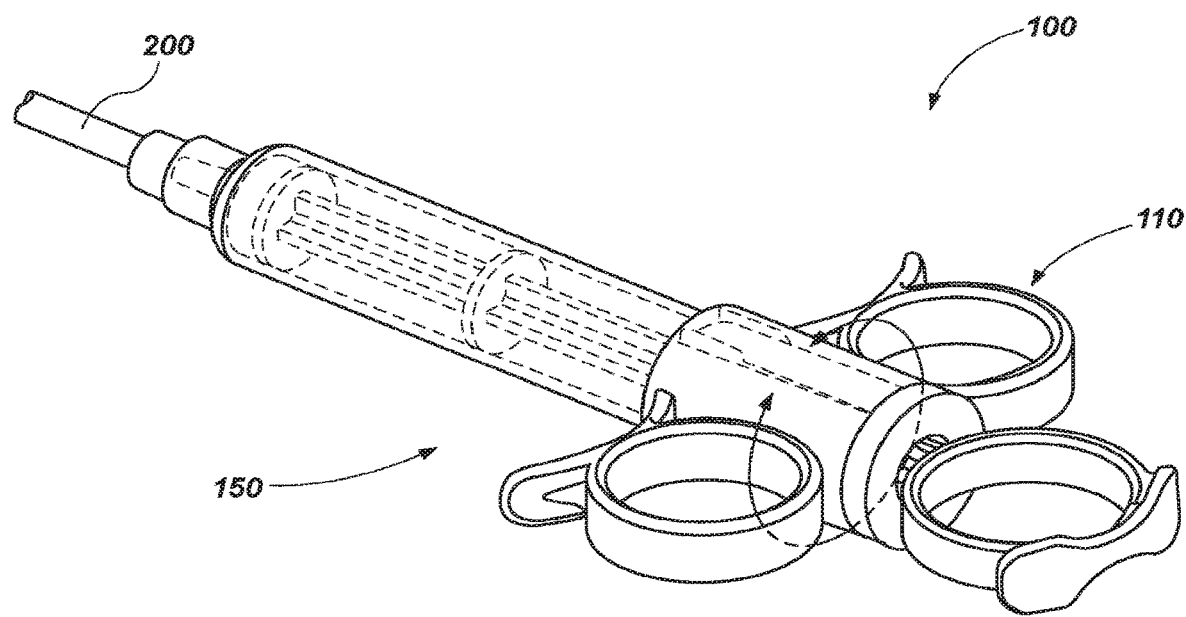

FIGS. 11A and 11B provide perspective views of a hand-held, hand-operated syringe 150 to which a finger control handle 110 has been assembled.

When the finger control handle 110 is installed on the barrel 152 of a syringe 150, relative configurations of features of the finger control handle 110 and the barrel 152 may enable the finger control handle 110 to rotate freely about the proximal portion 153 of the barrel 152. In a specific embodiment, the channel 113 through the body 112 of the finger control handle 110 and the proximal portion 153 of the barrel 152 may have cylindrical shapes. A clearance between the outer diameter (OD) of the proximal portion 153 of the barrel 152 and the inner diameter (ID) of the channel 113 through the body 112 of the finger control handle 110 may enable rotation of the finger control handle 110 about the circumference of the barrel 152 (e.g., coaxial rotation, about longitudinal axes through the channel 113 and the barrel 152). In various embodiments, the difference between the ID of the channel 113 and the OD of the proximal portion 153 of the barrel 152 may be about 0.010 inch or greater.

A syringe 150 that includes a finger control handle 110 that rotates freely about the barrel 152 of a syringe 150 may enable a physician or another healthcare provider to move his or her hand while handling the syringe 150, without transferring the rotational movement to a catheter 200 or another elongated medical instrument that has been secured to the syringe 150. As a result, a syringe 150 with a freely rotating finger control handle 110 may eliminate the need for rotating luer lock connectors, along with the cost and the potentially devastating consequences (e.g., introducing of air into the catheter, etc.) associated with use of rotating luer lock connectors.

In addition, free rotation of a finger control handle 110 around the barrel 152 of a syringe 150 will enable a physician or another healthcare provider to secure the barrel 153 to a fixed luer lock connector at a proximal end of a catheter 200 or another elongated medical instrument without rotating the catheter 200 or other elongated medical instrument, and without the requiring the physician or other healthcare provider to avoid the finger control handle 110 while rotating the barrel 152 of the syringe 150. Free rotation of the finger control handle 110 around the barrel 152 also enables the physician or other healthcare provider to place the finger control handle 110 in a comfortable orientation regardless of the initial orientations of the barrel 152 and the catheter 200 or other elongated medical instrument relative to one another, and enables the physician to move his or her hand intentionally or inadvertently without rotating the barrel 152 or the catheter 200 or other elongated medical instrument during a procedure.

In addition, a finger control handle 110 that rotates freely around a barrel 152 of a syringe 150 enables the finger control handle 110 to rest flat, and stably, upon a surface (e.g., a table, a tray, etc.) on which a physician or another healthcare provider places the syringe 150, regardless of the rotational orientation of the barrel 152 relative to a catheter 200 or other elongated medical instrument, and regardless of the rotational orientation of the barrel 152 to the surface.

Although the preceding disclosure provides many specifics, these should not be construed as limiting the scope of any of the ensuing claims. Other embodiments may be devised which do not depart from the scopes of the claims. Features from different embodiments may be employed in combination. The scope of each claim is, therefore, indicated and limited only by its plain language and the full scope of available legal equivalents to its elements.

What is claimed:

1. A medical system, comprising:
    a syringe, including:
        a barrel with a proximal end and a distal end, the barrel capable of receiving and retaining fluid and of fluid communication with a lumen of an elongated medical instrument to enable delivery of fluid to a patient and/or withdrawal of fluid from the patient, the barrel including:
            a collar at or near the proximal end, the collar including a distally facing surface outside of an outer circumference of a remainder of the barrel; and
            a plurality of discrete distal retention elements positioned at different radial positions around a circumference of the barrel, each distal retention element protruding from an intermediate location on the barrel and including a proximally facing surface, the proximally facing surface comprising a substantially planar surface, at least one distal retention element of the plurality of discrete distal retention elements tapering distally toward the outer circumference of the remainder of the barrel from the proximally facing surface to a more distal location along a length of the barrel; and
            a proximal portion defined between the collar and the at least one distal retention element; and
        a plunger insertable into and removable from an interior of the barrel; and
    a finger control handle separate from the syringe and capable of assembly directly with the barrel of the syringe, the finger control handle including:
        a body with a channel capable of receiving the barrel and of residing over the proximal portion of the barrel in a manner that enables the finger control handle to rotate freely about a circumference of the proximal portion of the barrel while forcing the plunger distally into the barrel to expel fluid from the barrel and/or while forcing the plunger proximally out of the barrel;
        a plurality of tabs at locations around the body of the finger control handle that correspond to different radial positions of the plurality of discrete distal retention elements around the circumference of the barrel of the syringe, and
        a pair of finger loops located on opposite sides of the body.

2. The medical system of claim 1, wherein the plurality of tabs of the finger control handle includes at least one flexible tab that corresponds to the at least one distal retention element, the at least one flexible tab configured to flex outward as the at least one flexible tab slides over the at least one distal retention element and to resiliently move back to an original position when an entirety of the body of the finger control handle is positioned over the proximal portion of the barrel of the syringe.

3. The medical system of claim 1, further comprising:
    at least one elongated medical instrument configured to be coupled to a distal end of the barrel in such a way that the at least one elongated medical instrument rotates with the barrel of the syringe.

4. The medical system of claim 2, wherein the at least one flexible tab is further configured to be pulled outward to enable the body of the finger control handle to intentionally be moved distally off of the proximal portion of the barrel of the syringe.

5. The medical system of claim 2, wherein the at least one flexible tab includes an inward protrusion that is configured to abut against the proximally facing surface of the at least one distal retention element.

6. The medical system of claim 3, wherein the at least one elongated medical instrument comprises a catheter.

7. A medical system, comprising:
a syringe with a barrel that includes:
- a collar at or near a proximal end of the barrel, the collar including a distally facing surface outside of an outer circumference of a remainder of the barrel; and
- a plurality of distal retention elements protruding from intermediate locations around a circumference of the barrel, each distal retention element tapering distally toward the outer circumference of the remainder of the barrel from a substantially planar proximally facing surface to a more distal location along a length of the barrel,
- an interior of the barrel being capable of receiving fluid and retaining the fluid; and a handle provided separately from the barrel and capable of assembly directly on an outer surface of the barrel, between the collar and the plurality of distal retention elements, the handle including a body capable of free rotation around a circumference of the barrel when the handle is assembled with the barrel and while forcing a plunger of the syringe distally into the barrel to expel fluid from the barrel and/or while forcing the plunger proximally out of the barrel to draw fluid into the barrel, the handle further including a plurality of tabs at locations around the body that flexibly engage the plurality of distal retention elements of the barrel of the syringe; and an elongated medical instrument coupled to a distal end of the barrel in such a way that rotation of the barrel will rotate the elongated medical instrument, a lumen of the elongated medical instrument in fluid communication with the interior of the barrel.

8. The medical system of claim 7, wherein the elongated medical instrument comprises a catheter.

* * * * *